United States Patent [19]

Doemland

[11] Patent Number: 4,754,763

[45] Date of Patent: Jul. 5, 1988

[54] NONINVASIVE SYSTEM AND METHOD FOR TESTING THE INTEGRITY OF AN IN VIVO BONE

[75] Inventor: Harvey H. Doemland, Lawrence, Kans.

[73] Assignee: Noninvasive Technology, Inc., Portland, Oreg.

[21] Appl. No.: 64,107

[22] Filed: Jun. 17, 1987

[51] Int. Cl.$^4$ .............................................. A61B 5/00
[52] U.S. Cl. ..................................... 128/739; 128/774
[58] Field of Search ............... 128/653, 739, 740, 774, 128/782; 73/579, 582, 588; 324/58 A, 58.5 A

[56] References Cited

U.S. PATENT DOCUMENTS

| | | | |
|---|---|---|---|
| 3,477,422 | 11/1969 | Jurist, Jr. et al. | 128/774 |
| 4,048,986 | 9/1977 | Ott | 128/653 |
| 4,235,243 | 11/1980 | Saha | 128/774 X |
| 4,416,269 | 11/1983 | Enomoto et al. | 128/739 X |
| 4,421,119 | 12/1983 | Pratt, Jr. | 128/774 X |
| 4,649,933 | 3/1987 | Jackson | 128/774 |
| 4,688,580 | 8/1987 | Ko et al. | 128/653 X |

OTHER PUBLICATIONS

Markey, E. L. and Juist, J. M., (1974), Tibial Resonant Frequency Measurements as an Index of Strength of Fracture Union, Wisconsin Medical Journal, 73, pp. 62-65.

Lewis, Jack L., (1975), A Dynamic Model of a Healing Fractured Long Bone, Journal of Biomechanics, 8, pp. 17-25.

Collier, R. J., Nadav, O. and Thomas, T. G., (1982), The Mechanical Resonances of a Human Tibia: Part I-in vitro, Journal of Biomechanics, 15, 8, pp. 545-553.

Sonstegard, D. A. and Matthews, L. S., (1976), Sonic Diagnosis of Bone Fracture Healing, Journal of Biomechanics, 9, pp. 689-694.

Hirayama, T. and Sekiguchi, T., (1979), Assessment of Fracture Healing by Vibration, Acta Ortho. Scand., 50, pp. 391-398.

White, A. A., Panjabi, M. M. and Southwick W. O., (1976), The Four Biomechanical Stages of Fracture Repair, Engineering Laboratory for Musculoskeletal Diseases, Section of Orthopedic Surgery (Yale University School of Medicine, New Haven, Conn.).

Doemland, H. H. and Stanley, B., (1979), A Method to Monitor the Healing of Human Long Bones, IEEE Frontiers of Engineering in Health Care, IEEE/Engineering in Medicine and Biology Society First Annual Conference.

Doemland, H. H., Assessment of Fracture Healing of Long Bones Using the Spectral Content of the Impulse Response, Trans. Ortho. Res. Soc. 7.

Jacobs, Rae R., Doemland, H. H., Konijeh, J. R. and Kliethermes, J., (1983), Assessment of Bone Healing by Radiography, Dynamic Bone Scanning and Resonant Frequency Analysis Trans. of the Orto. Res. Soc. 8.

Primary Examiner—Ruth S. Smith
Attorney, Agent, or Firm—Chernoff, Vilhauer, McClung & Stenzel

[57] ABSTRACT

A noninvasive method of testing the integrity of an in vivo bone, to determine either the possible existence of a fracture or the progress of healing of a fracture, comprises placing an electrical vibration transducer against the exterior of the soft tissue surrounding the bone, including a mechanical vibration in the bone by striking it with a reflex hammer, and producing an electrical signal from the transducer representative of the mechanical vibration thus induced in the bone. The resonant frequency and the energy concentration at the resonant frequency exhibited by the mechanical vibration are both determined from the electrical signal, and first visual indicia variably responsive to the resonant frequency and second visual indicia variably responsive to the energy concentration are displayed. Preferably, these are both normalized indicia representing ratios between the resonant frequency and energy concentration, respectively, of the tested bone and respective reference values representative of the resonant frequency and energy concentration, respectively, of a known intact bone of the same type. Such testing is performed at different times during the fracture healing process, and the results of the different tests are displayed simultaneously to show progress. Apparatus for carrying out the process is also disclosed.

18 Claims, 3 Drawing Sheets

INTACT TIBIA

FRACTURED TIBIA

INTACT TIBIA $F_{rn} = \dfrac{F_{rf}}{F_{ri}}$ = NORMALIZED RESONANT FREQUENCY $ECV_n = \dfrac{A_{rf}/A_{tf}}{A_{ri}/A_{ti}}$ = NORMALIZED ENERGY CONCENTRATION VALUE

NONINVASIVE SYSTEM AND METHOD FOR TESTING THE INTEGRITY OF AN IN VIVO BONE

BACKGROUND OF THE INVENTION

This invention relates to the testing of the integrity of in vivo bones to determine either the possible existence of a fracture or the progress of healing of a fracture. More particularly, the invention relates to a system for testing the integrity of such bones noninvasively by inducing a mechanical vibration in the bone, detecting the vibration by means of an electrical vibration transducer, producing an electrical signal representative of the vibration, and analyzing the vibration from the electrical signal.

In current medical practice, a number of techniques are used to detect bone fractures and to evaluate the healing progress of a fracture. Fracture detection techniques include examination of X-rays and radio isotope scanning. Fracture healing evaluation techniques include observation of stability of the bone, knowledge of the patient's history, and examination of X-rays of the fracture. All of these measures require substantial experience and involve subjective evaluation of the state of the bone. As a result, small or partial fractures such as stress fractures are sometimes undetected, while some non-unions are identified too late in the healing evaluation process for timely surgical intervention. Accordingly, a more objective measure of the existence of a fracture and of the healing state of a fractured bone would be a useful clinical tool.

A number of biomedical researchers have explored various measures of the mechanical properties of bone. Prior researchers modeled bones as beams, evaluating them under a variety of boundary conditions and loading and predicting a hyperbolic relationship between rigidity of a fracture callous and the percentage of healing. Others developed and tested conceptual models of the human ulna to be used in the prediction of ulnar resonant frequency. Markey and Jurist in 1974 suggested that the natural frequency of the tibia could be used as an index of fracture healing. Lewis in 1975 presented a dynamic model of a healing fractured long bone and asserted that the peak response of an accelerometer attached to a healing bone was a measure of its stiffness. Collier et al. in 1982 presented theoretical models and experimental verification of the mechanical resonances of the human tibia in vitro. Others found a correlation between the transmission coefficient of elastic waves traveling through the fracture site and the degree of union. Sonstegard and Matthews in 1976 reported on the impulsive time responses of fractured bones, while Hirayama and Sekiguchi in 1979 used the frequency response and the time waveform of the impulse response. White et al. in 1976 reported that a normally healing fracture shows a sudden increase in stiffness as the fracture callous changes from soft tissue to bone. However, all of the foregoing mechanical techniques were invasive, or time-consuming and complicated, or all of these. They did not suggest how to obtain reliable results quickly by noninvasive testing of in vivo bones.

The present inventor, in conjunction with others, has previously suggested use of the spectral content of the pulse response of in vivo long bones in the evaluation of fracture healing, and has presented results of such spectral content using a noninvasive technique and a microprocessor-based signal analyzer to obtain the Fourier transform of the pulse response from which the predominant resonant frequency can be determined, as set forth in articles published in 1979, 1982 and 1983. These articles point out that a fractured bone will have a different spectral content of the pulse response than a healthy contralateral bone of the same type, and that the spectral content of the fractured bone should approach that of the healthy bone as healing progresses. The resonant frequency indicated by the predominant peak of the Fourier transform is the most easily recognizable feature of the spectral content for purposes of comparing the fractured bone with the healthy bone.

If the foregoing spectral content comparison technique could yield consistent results, there would be no need for improving upon it. However, numerous factors combine to make the results inconsistent. For example, although the resonant frequency is proportional to stiffness of the bone which, in turn, is indicative of bone integrity and progress of healing, the resonant frequency is also inversely proportional to such factors as mass and damping. Accordingly, factors other than stiffness which can affect the resonant frequency exhibited by the pulse response of an in vivo bone include a large amount of callous formation from healing which adds mass to the system, and synostosis which couples another bone into the system (such as coupling the fibula to a healing tibia). Moreover, the amount of muscle and other soft tissue surrounding a bone affects both the mass and the damping of the system, thereby also affecting its resonant frequency in a manner unrelated to the stiffness of the bone. Although the latter variables could theoretically be compensated for by comparison of the spectral content of the pulse response of the tested bone to that of a healthy corresponding contralateral bone, other variables such as possible unavailability of an intact contralateral bone, different testing techniques by different operators, and different muscle tension of the respective limbs during testing, make the magnitude of the resonant frequency alone too unreliable an indicator to yield consistently accurate results.

SUMMARY OF THE PRESENT INVENTION

The present invention provides a noninvasive method and apparatus for obtaining and utilizing the pulse response of an in vivo bone in such a way that its integrity, either with respect to the possible existence of a fracture or with respect to its progress in healing a fracture, can be determined objectively with consistent reliability.

An electrical vibration transducer, such as a microphone, is placed adjacent to the bone under test and a mechanical vibration is induced in the bone by imparting an exciting force thereto, such as by striking it with a reflex hammer. The resultant electrical signal from the transducer, which is representative of the mechanical vibration induced in the bone, is used to determine not only the magnitude of the resonant frequency of the induced vibration but also the concentration of energy at the resonant frequency compared to the other frequencies exhibited by the induced vibration, preferably by calculating the Fourier transform thereof. First and second visual indicia, variably responsive to the magnitude of the resonant frequency and to the magnitude of the energy concentration value (ECV), respectively, are then displayed. Preferably, these are displayed simultaneously so that their relative magnitudes can be compared visually. Also, they are preferably displayed in a manner which compares them to respective reference values representing the resonant frequency and energy concentration value obtained by similar testing of a corresponding contralateral intact bone of the patient (if available) or, alternatively, values representing typical intact bones of the same type and surrounded by the same amount of soft tissue derived from a data base of a large sample population. Such comparative indicia may be conveniently presented as "normalized" ratios between the values for the bone under test and the corresponding values for the intact bone.

Furthermore, when monitoring the healing of a fractured bone, resonant frequency and energy concentration indicia for the bone can be obtained at time intervals during the healing process, and displayed as multiple indicia simultaneously, each correlated to the time when the testing was performed so that a trend can be easily discerned. Such time-related indicia can then be compared to target values representative of full healing so that their approach to, and arrival at, the target values can be monitored. A planar Cartesian coordinate system, wherein one axis represents resonant frequency indicia and the other axis represents energy concentration indicia, with a point or points displayed thereon representing both such indicia, is particularly helpful as a diagnostic tool.

The present invention reflects a recognition that the concentration of energy at the resonant frequency exhibited by the pulse response of a fractured or incompletely healed in vivo bone is generally less than that of an intact, corresponding contralateral in vivo bone of the same patient. Because the system of the present invention combines the magnitude of energy concentration with the magnitude of resonant frequency as an indicator of the integrity of an in vivo bone, the adverse effects of the previously-described variables, which cause resonant frequency alone to be an unreliable indicator of bone integrity, are substantially reduced. Although testing for energy concentration is also subject to variables, and therefore also would be incapable by itself of producing consistently reliable results, the combination of variables affecting energy concentration is different from the combination of variables affecting resonant frequency. Accordingly, the combination of the two indicators yields objective results of significantly greater consistency and reliability than would either indicator individually.

Although the energy concentration exhibited by a bone's pulse response could theoretically be determined in different ways, it is most accurately determined from the Fourier transform of the induced vibration. This can be done by calculating the ratio between the area beneath the predominant or resonant peak of the Fourier transform curve and the total area beneath the curve.

Likewise, the resonant frequency is determinable from the Fourier transform by identification of the predominant peak, and/or by means of the phase response.

The foregoing and other objectives, features, and advantages of the invention will be more readily understood upon consideration of the following detailed description of the invention, taken in conjunction with the accompanying drawings.

DESCRIPTION OF THE PREFERRED EMBODIMENT

Figure 1:
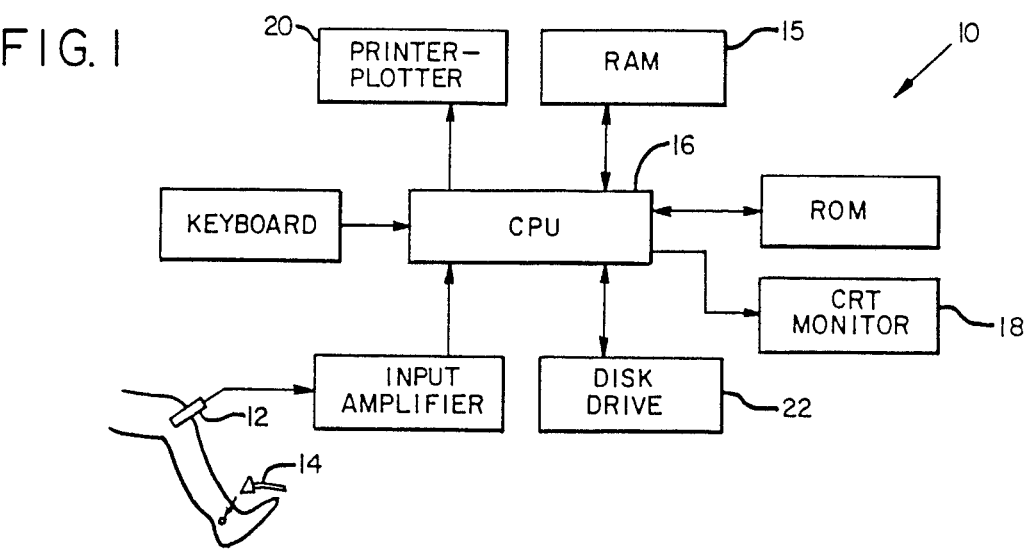
FIG. 1 is a block diagram of an exemplary spectrum analyzer system for determining the integrity of an in vivo bone in accordance with the present invention.

With reference to FIG. 1, the system of the present invention employs conventional spectrum analyzer hardware, indicated generally as 10, in an unconventional manner pursuant to unique programming to test the integrity of in vivo bones noninvasively. An electrical input signal is generated from a vibration transducer such as a crystal microphone 12 placed adjacent to the bone under test, such as a tibia as shown. The microphone is placed directly in contact with the skin, without penetrating any tissue, at a suitable monitoring point such as the tibial plateau or anterior medial aspect of the proximal tibia. Excitation is imparted by gently striking the medial malleolus with a percussion or reflex hammer 14. The mechanical vibration thus induced in the bone is transmitted directly to the crystal of the microphone via a plastic pedestal (not shown) which is integral to the microphone, thus avoiding an air interface. Although testing of the tibia is illustrated, the system can be used with equal effectiveness with respect to all of the long bones such as the humerus, radius, ulna, femur and fibula, as well as other bones (human or animal), by placing the microphone adjacent to one extremity of the bone and inducing a mechanical vibration by striking the bone adjacent its opposite extremity, all without penetrating the soft tissue surrounding the bone.

The electrical signal emitted by the microphone is representative of the mechanical vibration induced in the bone by the striking pulse. At least four such vibrations are preferably induced in succession to constitute a single patient test, and the resultant time record of each induced vibration is stored in the RAM 15. As each such time record is stored, a CPU 16, which may be a conventional INTEL 8085, computes a 256-point fast Fourier transform of the vibration and stores it in the RAM. If desired, each time record and its spectral content (Fourier transform) may be displayed on a CRT monitor 18 or printed on a printer-plotter 20, both of which are capable of displaying both graphics and alphanumerics. After four such records are obtained they may be permanently stored on magnetic disk by means of disk drive 22.

Once all four records are stored in RAM, the average Fourier transform of the four records is preferably calculated in a conventional manner. From this average Fourier transform the average resonant frequency of the induced vibration is determined by identifying the predominant peak of the Fourier transform, and the magnitude of the energy concentration value (ECV) is determined by calculating the ratio between the area beneath the predominant peak of the Fourier transform curve and the total area beneath the curve.

Figure 2A:
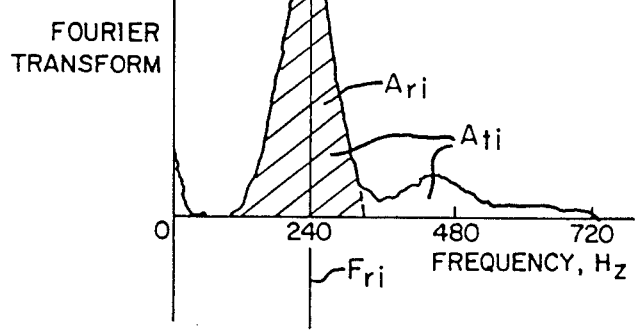
FIG. 2A is an illustrative Fourier transform curve of the pulse response of an in vivo intact tibia.
Figure 2B:
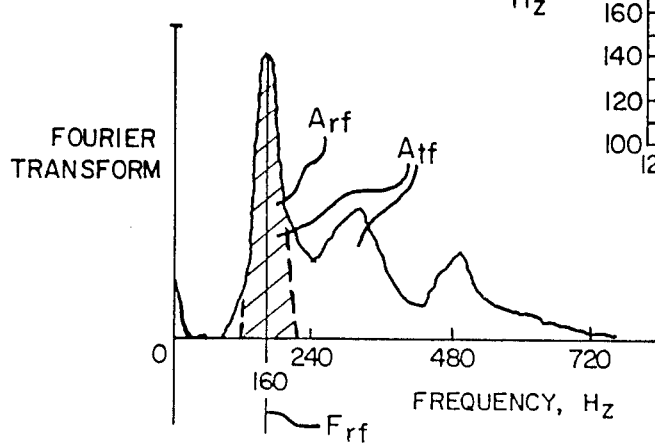
FIG. 2B is an illustrative Fourier transform curve of the pulse response of an in vivo fractured tibia.
Figure 3:
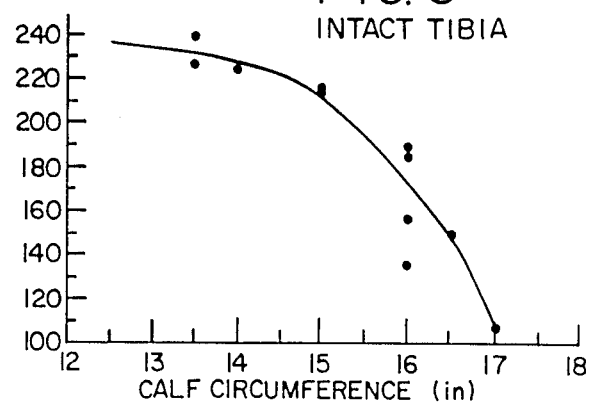
FIG. 3 is a graph illustrating how the resonant frequency exhibited by the pulse response of an intact tibia might be expected to vary with a patient's calf circumference.

For example, FIG. 2A illustrates how a typical Fourier transform curve for a healthy, intact tibia might appear, while FIG. 2B illustrates how a typical Fourier transform curve for a contralateral tibia having an unhealed fracture might appear. The predominant peak for the intact bone is at about 240 Hz, while the predominant peak for the fractured bone is at a substantially lower frequency, e.g. approximately 160 Hz. These are the respective resonant frequencies $F_{ri}$ and $F_{rf}$ of the intact and fractured tibias, respectively. If no contralateral intact tibia were available, the frequency $F_{ri}$ could alternatively be taken from a curve such as FIG. 3 for a calf circumference corresponding to that of the patient. These curves would be derived from a data base of a large sample population for each type of bone.

The area $A_{ri}$ under the predominant peak for the intact tibia of FIG. 2A represents a significantly greater percentage of the total area $A_{ti}$ under the Fourier transform curve than does the area $A_{rf}$ under the predominant peak for the fractured tibia of FIG. 2B, relative to the total area $A_{tf}$. This indicates that significantly more of the energy of the induced vibration is concentrated at the resonant frequency for the intact bone than for the fractured bone, due to differences in damping and modes of vibration for the intact bone and fractured bone, respectively. The energy concentration value for each bone can be quantified by the ratio between the area under the predominant peak and the area under the entire Fourier transform curve for each bone, although other calculation methods could be used as well. The area under the peak is determined by projecting the slope of the curve on both sides of the peak downwardly as shown in FIGS. 2A and 2B. If a secondary frequency should obscure the slope of the curve on one side of the resonant frequency, such slope may be considered to be symmetrical to that on the opposite side for purposes of projecting the two slopes to compute the areas $A_{ri}$ and $A_{rf}$, respectively. In the system of the present invention, it is most convenient to quantify the energy concentration values by means of the ratios $A_{ri}/A_{ti}$ and $A_{rf}/A_{tf}$, respectively. In this way the intact bone has both the higher value with respect to resonant frequency and the higher value with respect to energy concentration to facilitate the comparison of the bone under test with the contralateral intact bone. For those cases where a contralateral intact bone is not available, the factor $A_{ri}/A_{ti}$ can be taken from a curve representing a large sample data base comparable to the curve of FIG. 3.

Although the resonant frequency and energy concentration values for the fractured bone and intact bone, respectively, could be displayed as separate values side-by-side for comparison purposes, it is more convenient to compare them by displaying the values for the fractured bone as "normalized" values relative to the corresponding values for the intact bone. Thus, the normalized resonant frequency $F_{rn}$ for the fractured bone can be displayed as a single value equal to the ratio between the resonant frequency for the fractured bone and the resonant frequency for the intact bone, e.g. $F_{rf}/F_{ri}$.

Similarly, the normalized energy concentration value $ECV_n$ for the fractured bone can be displayed as a single value equal to the ratio between the energy concentration value for the fractured bone and the energy concentration value for the intact bone, e.g. $(A_{rf}/A_{tf})/(A_{ri}/A_{ti})$.

Ideally, then, if a bone under test is not fractured or is fully healed from a fracture, its normalized resonant frequency and energy concentration values should both equal approximately unity. Conversely, if the bone is fractured or incompletely healed, the normalized values should both be less than unity. As multiple tests are performed on a healing bone at intervals to monitor its healing progress, both values should tend to increase progressively, from smaller values less than unity immediately following the fracture to larger values approaching unity. If such a trend during healing does not develop, a non-union is indicated calling for corrective procedures.

Figure 4:
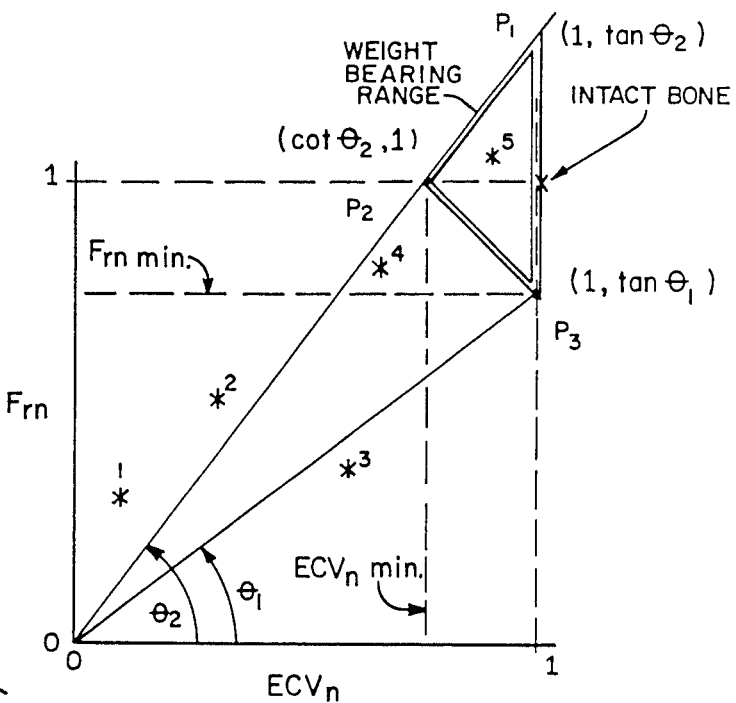
FIG. 4 is an illustrative Cartesian coordinate display of resonant frequency and energy concentration indicia for monitoring the healing of a typical fracture.

FIG. 4 illustrates a preferable mode by which the CRT monitor 18, and/or printer-plotter 20, can be employed to display both normalized values simultaneously for a bone under test so that an operator can immediately see how both values compare to unity. A planar Cartesian coordinate system is employed wherein the ordinate is the normalized resonant frequency value $F_{rn}$ and the abscissa is the normalized energy concentration value $ECV_n$. In such a display, test points falling near the upper right-hand corner corresponding to the values 1, 1 would indicate an intact or fully-healed bone. Conversely, points near the lower left-hand corner corresponding to the values 0, 0 would indicate a new fracture with little or no healing. Points in between would correspond to partial or incomplete fractures, or partially-healed fractures.

FIG. 4 illustrates the exemplary use of the coordinate system for monitoring the healing progress of a bone, wherein data points representing normalized test values at different times after fracture show a gradual migration from the 0, 0 value toward the 1, 1 value, indicating normal healing. Data point 1 is the point derived from testing immediately after the fracture. Data point 5 is the point derived from the final test. The numbers 1 through 5 are known by the operator to represent predetermined times after fracture, for example, at four-week intervals.

Figure 5:
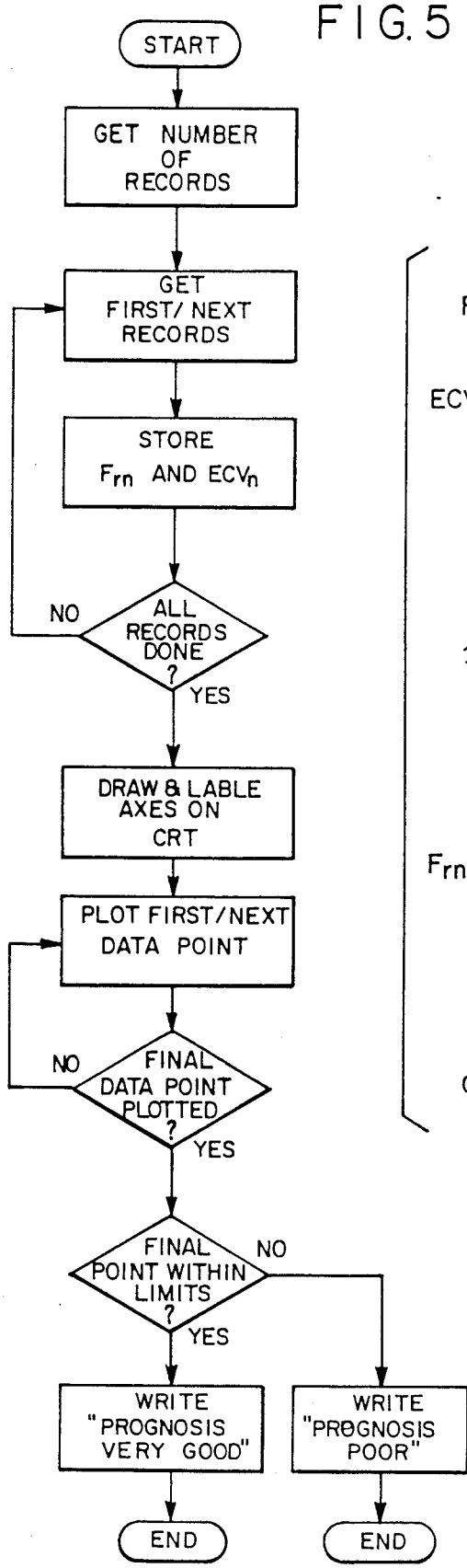
FIG. 5 is a simplified logic flow diagram illustrating how the CPU of the spectrum analyzer may be programmed to produce the Cartesean coordinate display of FIG. 4.

A zone in the area of the 1,1 value may, if desired, be displayed to aid in the visual determination of the integrity of the bone. Such a zone is depicted in FIG. 4 as the "weight bearing range" defined by the triangle P1, P2, P3. If, after a suitable healing time, the final data point falls within this range, the judgment is made that the bone is capable of bearing weight or stress. If, on the other hand, after a suitable time the data point falls outside the triangle, the judgment is made that the bone is not healing properly. The values of the angles $\theta 1$ and $\theta 2$ which define the triangle would be determined from the results of clinical trials with respect to each different type of bone. (The angles and other trigonometric values in FIG. 4 are shown only to define the triangle, and would not be part of the actual working display.) FIG. 5 depicts a simplified logic flow diagram by which the CPU 16 is programmed to display the graph of FIG. 4.

Figure 6A:
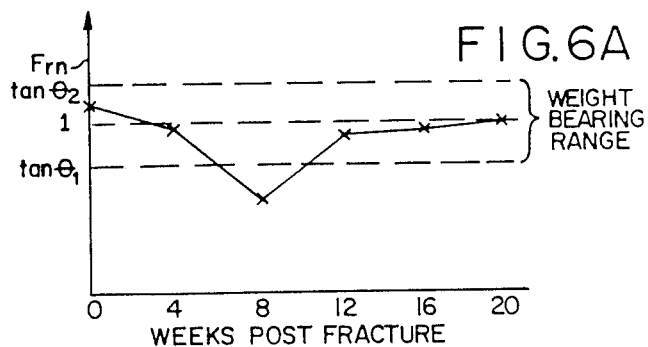
FIGS. 6A, 6B and 6C are illustrative time graphs for displaying resonant frequency and energy concentration indicia for monitoring the healing of a typical fracture.
Figure 6B:
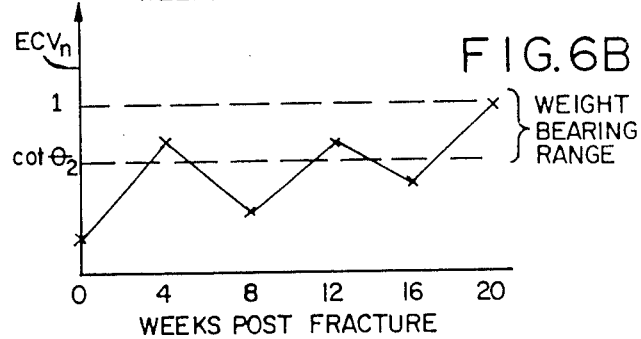
Figure 6C:
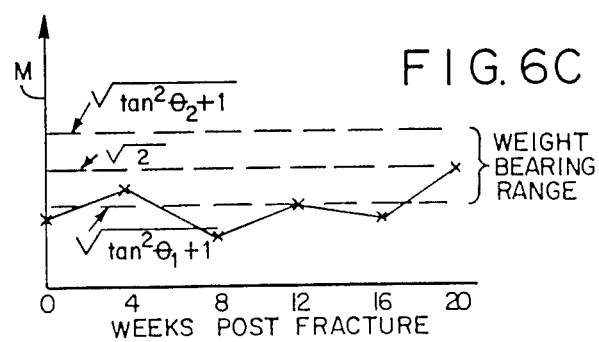

FIGS. 6A, 6B and 6C illustrate an alternative manner by which the CRT monitor 18 and/or printer plotter 20 could display the normalized resonant frequency and energy concentration values in a time graph format equivalent to the Cartesian coordinate format of FIG. 4.

Figure 7:
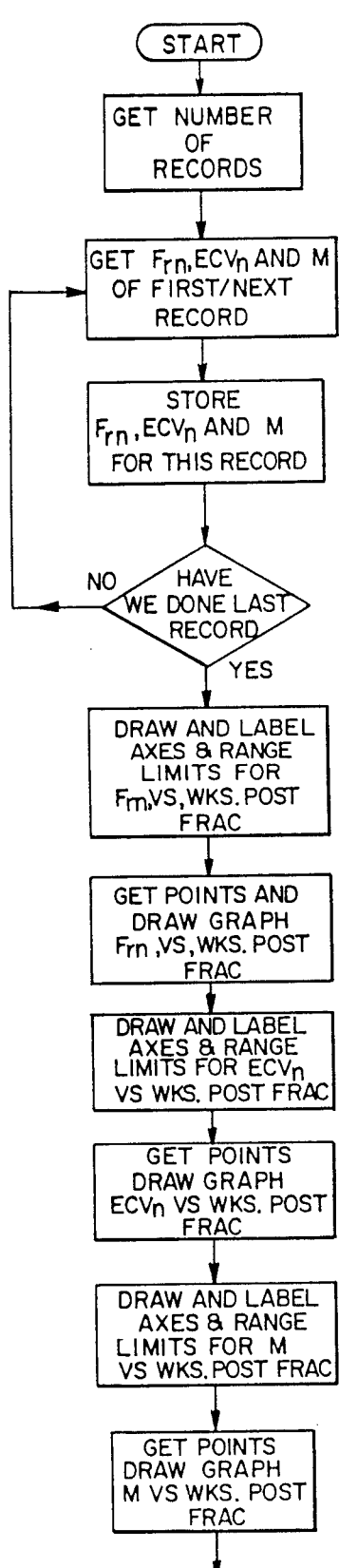
FIG. 7 is a simplified logic flow diagram illustrating how the CPU of the spectrum analyzer may be programmed to produce the time graph displays of FIGS. 6A, 6B and 6C.
Figure 7:
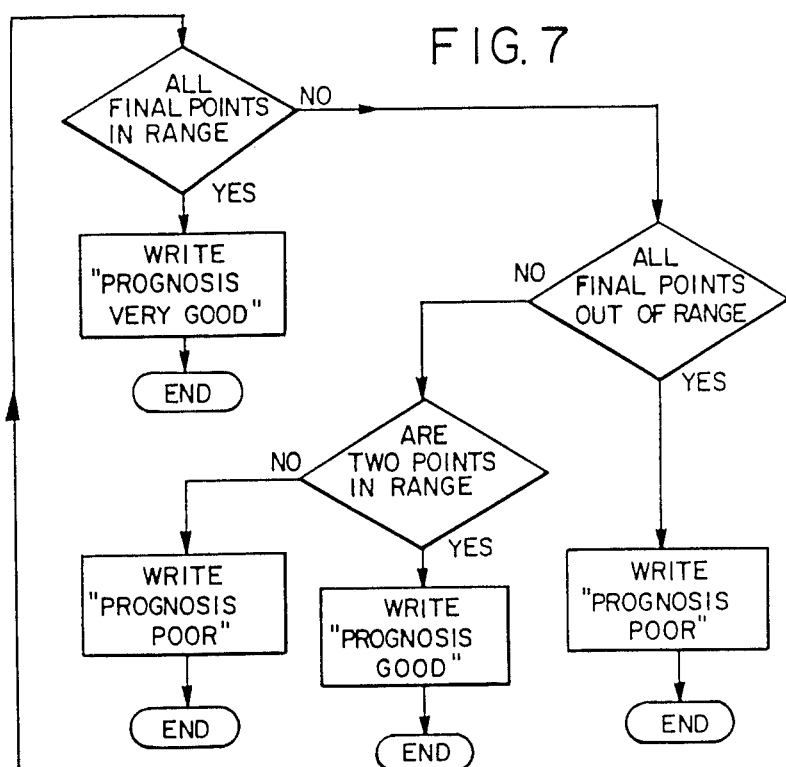

FIG. 6A plots the normalized resonant frequency $F_{rn}$ for a tested bone (different from the bone of FIG. 4) against time, while FIG. 6B plots its normalized energy concentration value $ECV_n$ against time. FIG. 6C plots the resultant vector M of these two normalized values, where $M = \sqrt{F_{rn}^2 + ECV_n^2}$. The "weight bearing range" corresponding to the triangle P1, P2, P3 of FIG. 4 is simply determined trigonometrically from FIG. 4. (Again, the trigonometric values shown define the range, but would not be part of the working display.) It should be noted that, for purposes of illustration, the normalized frequency $F_{rn}$ of FIG. 6A for the exemplary bone has been shown to fall within the weight-bearing range for all data points except the one at eight weeks. However, the normalized energy concentration value $ECV_n$ of FIG. 6B is only marginally within the weight-bearing range until the final data point, and the resultant vector M of FIG. 6C falls in the weight-bearing range only at four weeks and at the final data point. The anomaly, whereby the data points of FIGS. 6A, 6B and 6C all fall within the weight-bearing range at four weeks, can sometimes occur due to unusual combinations of the variables discussed previously, but would be immediately disregarded because of recognition that four weeks is much too soon for a complete healing of a fracture. The upward trend after eight weeks is significant in indicating proper healing progress, and the final data points at 20 weeks indicate complete healing. FIG. 7 illustrates a simplified logic flow diagram by which the CPU 16 is programmed to display the time graphs of FIGS. 6A, 6B and 6C.

The advantage of calculating and displaying the energy concentration exhibited by the pulse response of the bone, as well as its resonant frequency, is apparent when it is realized that the normalized resonant frequency values as displayed in FIGS. 4 and 6A may, in some cases, prematurely indicate an intact bone by approaching unity and, in some other cases, fail to approach unity even though the bone may be fully intact and/or the fracture fully healed, due to the variables mentioned previously. In such case the energy concentration value, and particularly the trend thereof with respect to time when monitoring fracture healing, when combined with the resonant frequency value and its trend, will normally yield definite and accurate, rather than equivocal or misleading, diagnostic information.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A noninvasive method of testing the integrity of an in vivo bone surrounded by soft tissue comprising:
   (a) placing an electrical vibration transducer adjacent to said bone without penetrating said tissue;
   (b) inducing a mechanical vibration in said bone by imparting an exciting force thereto without penetrating said tissue;
   (c) producing an electrical signal from said transducer representative of said mechanical vibration induced in said bone;
   (d) determining from said electrical signal the resonant frequency exhibited by said mechanical vibration;
   (e) determining from said electrical signal an energy concentration value, defined by energy at said resonant frequency relative to the magnitude of energy at other frequencies, exhibited by said mechanical vibration;
   (f) displaying a first visual indicium variably responsive to said resonant frequency and a second visual indicium variably responsive to said energy concentration value and
   (g) determining the integrity of said bone from said displayed first and second inidicia.

2. The method of claim 1 wherein said step (f) comprises displaying both said first visual indicium and said second visual indicium simultaneously.

3. The method of claim 1, comprising repeating steps (a) through (e) inclusive at different times with respect to the same bone, wherein said step (f) comprises displaying said first visual indicium and said second visual indicium each as one of a series of first visual indicia and second visual indicia, respectively, each of said first visual indicia and second visual indicia corresponding to a different time of performance of said steps (a) through (e) inclusive.

4. The method of claim 1 wherein said step (f) comprises displaying said first visual indicium in the form of a comparison between said resonant frequency and a reference value.

5. The method of claim 4 wherein said step (f) comprises displaying said first visual indicium as a value equal to a ratio between said resonant frequency and said reference value.

6. The method of claim 1 wherein said step (f) comprises displaying said second visual indicium in the form of a comparison between said energy concentration value and a reference value.

7. The method of claim 6 wherein said step (f) comprises displaying said second visual indicium as a value equal to a ratio between said energy concentration value and said reference value.

8. The method of claim 1 wherein said step (e) comprises determining from said electrical signal the Fourier transform of said mechanical vibration, and determining said energy concentration value from said Fourier transform.

9. The method of claim 1 wherein said step (f) comprises displaying said first visual indicium and said second visual indicium as a pair of values represented by a point on a Cartesian coordinate graph, one axis of which represents a value responsive to said resonant frequency and the other axis of which represents a value responsive to said energy concentration value.

10. Apparatus for noninvasively testing the integrity of an in vivo bone surrounded by soft tissue. comprising:
   (a) means for inducing a mechanical vibration in said bone;
   (b) an electrical vibration transducer means for producing an electrical signal representative of said mechanical vibration induced in said bone;
   (c) means responsive to said electrical
   signal for determining the resonant frequency exhibited by said mechanical vibration, and for determining an energy concentration value, defined by the magnitude of energy at said resonant frequency relative to the magnitude of energy at other frequencies, exhibited by said mechanical vibration; and (d) display means for displaying a first visual indicium variably responsive to said resonant frequency and a second visual indicium variably responsive to said energy concentration value, whereby the integrity of said bone is determined from said displayed first and second indicia.

11. The apparatus of claim 10 wherein said display means includes means for displaying both said first visual indicium and said second visual indicium simultaneously.

12. The apparatus of claim 10, further including data storage means for storing multiple different values responsive to multiple different resonant frequency values and multiple different energy concentration values, respectively, each determined from multiple different electrical signals produced at different times by said vibration transducer means, wherein said display means is responsive to said data storage means for simultaneously displaying multiple different first visual indicia, each variably responsive to a different resonant frequency value, and multiple different second visual indicia, each variably responsive to a different energy concentration value.

13. The apparatus of claim 10 wherein said display means comprises means for displaying said first visual indicium in the form of a comparison between resonant frequency and a reference value.

14. The apparatus of claim 13 wherein said display means comprises means for displaying said first visual indicium as a value equal to a ratio between said resonant frequency and said reference value.

15. The apparatus of claim 10 wherein said display means comprises means for displaying said second visual indicium in the form of a comparison between said energy concentration value and a reference value.

16. The apparatus of claim 15 wherein said display means comprises means for displaying said second visual indicium as a value equal to a ratio between said energy concentration value and said reference value.

17. The apparatus of claim 10 wherein said means responsive to said electrical signal includes means for determining from said electrical signal the Fourier transform of said mechanical vibration and determining said energy concentration value from said Fourier transform.

18. The apparatus of claim 10 wherein said display means comprises means for displaying said first visual indicium and said second visual indicium as a pair of values represented by a point on a Cartesian coordinate graph, one axis of which represents a value responsive to said resonant frequency and the other axis of which represents a value responsive to said energy concentration value.

* * * * *

UNITED STATES PATENT AND TRADEMARK OFFICE
CERTIFICATE OF CORRECTION

PATENT NO. : 4,754,763

DATED : July 5, 1988

INVENTOR(S) : Harvey H. Doemland

It is certified that error appears in the above-identified patent and that said Letters Patent is hereby corrected as shown below: Title page:

In the Abstract:
Line 6                  Change "including" to --inducing--

Col. 8, line 9          After "value" insert --;--

Col. 8, line 54         After "tissue" delete --.--

Col. 9, line 26         After "between" insert --said--

Signed and Sealed this

Twentieth Day of March, 1990

Attest:

JEFFREY M. SAMUELS

Attesting Officer

Acting Commissioner of Patents and Trademarks